(12) United States Patent
Kreindel

(10) Patent No.: US 7,643,883 B2
(45) Date of Patent: Jan. 5, 2010

(54) DEVICE AND METHOD FOR TREATING SKIN

(75) Inventor: Michael Kreindel, Haifa (IL)

(73) Assignee: Syneron Medical Ltd., Yokneam Illit (IL)

( * ) Notice: Subject to any disclaimer, the term of this patent is extended or adjusted under 35 U.S.C. 154(b) by 669 days.

(21) Appl. No.: 11/044,610

(22) Filed: Jan. 28, 2005

(65) Prior Publication Data

US 2006/0173518 A1 Aug. 3, 2006

(51) Int. Cl.
*A61F 2/00* (2006.01)
(52) U.S. Cl. ............................ 607/101; 607/99; 607/102
(58) Field of Classification Search ............. 607/96–99, 607/101, 102
See application file for complete search history.

(56) References Cited

U.S. PATENT DOCUMENTS

| 5,755,753 | A  | * | 5/1998  | Knowlton ................... 607/98 |
| 5,919,219 | A  |   | 7/1999  | Knowlton et al. |
| 5,938,657 | A  |   | 8/1999  | Assa et al. |
| 6,091,995 | A  | * | 7/2000  | Ingle et al. ................... 607/138 |
| 6,241,753 | B1 | * | 6/2001  | Knowlton ................... 607/99 |
| 6,413,255 | B1 | * | 7/2002  | Stern ........................ 606/41 |
| 6,702,808 | B1 |   | 3/2004  | Kreindel |
| 6,749,624 | B2 | * | 6/2004  | Knowlton ................... 607/104 |
| 6,749,626 | B1 |   | 6/2004  | Bhat et al. |
| 6,766,202 | B2 | * | 7/2004  | Underwood et al. .......... 607/99 |
| 7,278,991 | B2 | * | 10/2007 | Morris et al. ................. 606/41 |
| 2002/0002392 | A1 |   | 1/2002  | Bernabei |
| 2002/0043520 | A1 |   | 4/2002  | Bernabei |
| 2003/0032950 | A1 |   | 2/2003  | Altshuler et al. |
| 2005/0015125 | A1 | * | 1/2005  | Mioduski et al. ............ 607/102 |
| 2005/0131288 | A1 |   | 6/2005  | Turner et al. |
| 2005/0209193 | A1 | * | 9/2005  | Keller ........................ 514/64 |
| 2006/0173518 | A1 |   | 8/2006  | Kreindel |

\* cited by examiner

*Primary Examiner*—Roy D Gibson
(74) *Attorney, Agent, or Firm*—Browdy and Neimark, PLLC

(57) ABSTRACT

A system and method for heating a tissue volume under a skin surface of an individual from an initial temperature to a predetermined treatment temperature in the range of 42°-60° C. The method comprises applying electrodes to the skin surface and providing from the electrodes a continuous wave RF energy or a quasi-continuous wave RF energy, where the RF energy has a power selected to heat the tissue volume to the final temperature in an amount of time exceeding 0.5 sec. The system of the invention comprises electrodes and an RF generator configured to provide a continuous wave RF voltage energy or a quasi-continuous wave RF voltage across the electrodes where the RF energy has a power selected to heat the tissue volume to the final temperature in an amount of time exceeding 0.5 sec.

15 Claims, 2 Drawing Sheets

DEVICE AND METHOD FOR TREATING SKIN

FIELD OF THE INVENTION

This invention relates to methods and devices for treating skin.

BACKGROUND OF THE INVENTION

There are many medical and cosmetic treatments of skin that utilize heating a region of skin to be treated. Among these are hair removal, treatment of vascular lesions and skin rejuvenation. In these treatments, a volume of skin tissue under the skin to be treated is heated to a temperature that sufficiently high to achieve a desired effect, which is typically in the range of 45-60° C. One method that has been used for heating the epidermal and dermal layers of the skin is pulsed radio-frequency (RF) energy. In this method, electrodes are applied to the skin and an RF voltage pulse is applied across the electrodes. The properties of the voltage pulse are selected so as to generate an RF current pulse in the tissue to be treated that heats the tissue to the required temperature. For example, U.S. Pat. No. 6,749,626 discloses use of pulsed RF energy for inducing collagen formation in the dermis.

When an RF current pulse is used to heat a volume of skin tissue, the temperature of the tissue volume rises from body temperature to the required temperature within the duration of the pulse, which is typically less than 100 msec. The temperature of the tissue volume thus rises vary rapidly. Since the final temperature will actually depend on the electrical properties of the tissue volume which vary from individual to individual, the rapid rise in temperature of the tissue volume limits control of the tissue heating. Moreover, the rapid rise in temperature prevents the user from stopping the treatment should the tissue volume become overheated. Thus, using an RF pulse to heat the skin carries a risk of overheating the skin which could result in permanent scarring or other damage to the skin surface. Such damage to the skin includes, for example, a first degree or higher burn, blisters, or blood coagulation.

SUMMARY OF THE INVENTION

The present invention provides a method and system for heating a tissue volume under a skin surface. In accordance with the invention an RF current is generated in a tissue volume to be treated that heats the tissue volume to a desired temperature in a period of time that exceeds 0.5 sec. The slow rise in temperature allows the user to control the skin temperature and to avoid overheating of the skin. The invention is particularly useful for skin treatments requiring the tissue volume to be heated to a temperature in the range of 42° C. to 60° C. Such treatments include, for example, skin rejuvenation, collagen remodeling and contraction, skin tightening, wrinkle treatment, subcutaneous tissue treatment, cellulite treatment, pore size reduction, skin texture and tone improvement, acne treatment and hair removal.

In one embodiment of the invention, a pair of RF electrodes are applied to the skin surface, and an RF energy pulse is applied to the skin surface having a duration and power selected so as to heat the skin surface to a predetermined treatment temperature within an amount of time exceeding 0.5 sec. For example, an RF energy pulse having a power range of 2-10 Watts could be used. In this case a pulse duration of 0.5-1 sec would heat the tissue volume to a temperature in the range of 45°-60° C. within 0.5-2 sec. The electrodes could be positioned at a first location in a skin region to be treated and the RF energy pulse applied to the first location. The electrode pair could then be repositioned on the skin surface to another location in the region to be treated and the procedure repeated. In another embodiment of the invention, continuous wave (CW) RF energy is applied to the skin surface and by a pair of electrodes which are displaced over the skin surface. The power of the CW RF energy and the displacement speed are selected so that each of a plurality of successive tissue volumes are heated to the predetermined treatment temperature in a time that exceeds 0.5 sec as the electrodes pass on the skin surface over the tissue volume. For example, CW RF energy having a power range of 2-10 Watts could be used. In this case, a displacement speed of about 0.5-1.0 cm/sec would heat a tissue volume under the electrodes to a temperature in the range of 42°-60° C. in a time that exceeds 0.5 sec. Quasi-CW RF energy may also be used in which a train of RF pulses is applied to the skin surface, where the train has a frequency and the pulses have durations and powers, so as to heat the tissue volume to be treated to a predetermined temperature in a period of time that exceeds 0.5 sec.

The system of the invention comprises a two or more RF electrodes and an RF generator configured to apply an RF voltage across at least a pair of electrodes, where the RF voltage has a power selected to heat a tissue volume to a predetermined treatment temperature in a time period that exceeds 0.5 sec., when an electrode pair is applied to the skin surface over the tissue volume. The RF generator may be configured to deliver a pulse of RF energy having a duration exceeding 0.5 sec. Alternatively, the RF generator could be configured to deliver CW or quasi-CW RF energy to the electrodes, in which case, the electrodes are displaced over the skin surface during delivery of the RF energy. In a preferred embodiment of the system, a pair of RF electrodes are included in a hand held applicator. A user treating his own skin with the system of the invention may simply displace the applicator over the skin surface in the region to be treated at a speed at which the user feels that the skin is heated but not to an extent that causes pain to the user.

The slow heating of the skin volume by the method and system of the invention permits greater control of the tissue heating, and thus reduces the risk of overheating, and hence damaging, the tissue.

Thus, in its first aspect, the invention provides a system for heating a tissue volume under a skin surface of an individual from an initial temperature to a predetermined treatment temperature in the range of 42°-60° C., comprising:

(a) an applicator;
(b) a first electrode and a second electrode, at least the first electrode being associated with the applicator; and
(c) An RF generator configured to provide a continuous wave RF voltage energy or a quasi-continuous wave RF voltage across the first and second electrodes, the RF voltage selected to heat the tissue volume to the treatment temperature in a time period exceeding 0.5 sec.

In its second aspect, the invention provides a method for heating a tissue volume under a region of a skin surface of an individual from an initial temperature to a predetermined treatment temperature, the treatment temperature being in the range of 42°-60° C., comprising, for each of one or more locations in the region of the skin surface:

(a) applying a first electrode and a second electrode to the skin surface, at least the first electrode being applied to the location in the skin region;
(b) providing from the electrodes a continuous wave RF energy or a quasi-continuous wave RF energy to the tissue volume at the location, the RF energy having a power selected to heat the tissue volume at the location to the final temperature in an amount of time exceeding 0.5 sec.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
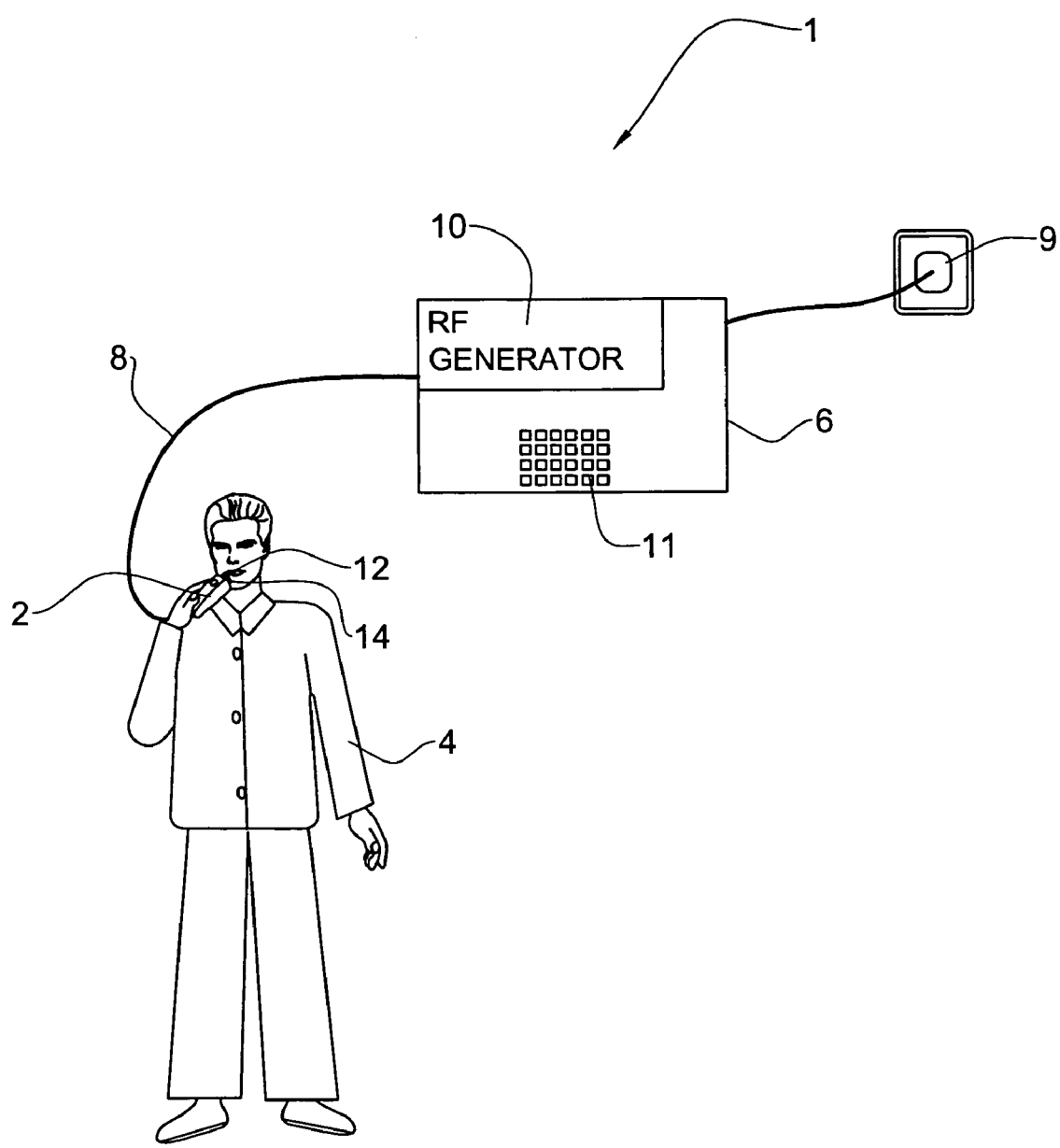
FIG. 1 shows a system for treating skin in accordance with one embodiment of the invention.

FIG. 1 shows a system 1 for treating skin in accordance with one embodiment of the invention. The system 1 includes a hand held applicator 2 that is used to apply RF energy to the skin of an individual 4. The applicator 2 is connected to a control unit 6 via a harness 8. The control unit 6 includes an RF generator 10 that generates a continuous wave, or quasi-continuous RF voltage across a pair of electrodes 12 and 14 in the applicator 2. The control unit 10 includes an input device such as a key pad 11 for selecting the wavelength and amplitude of the RF voltage generated by the RF generator 10 as required in any particular skin treatment. The RF generator is connected to the electrodes 12 and 14 by a pair of wires in the harness 8. The system 1 may be plugged into a wall electrical socket 9, as shown in FIG. 1 or use batteries (not shown) that are preferably rechargeable.

Figure 2:
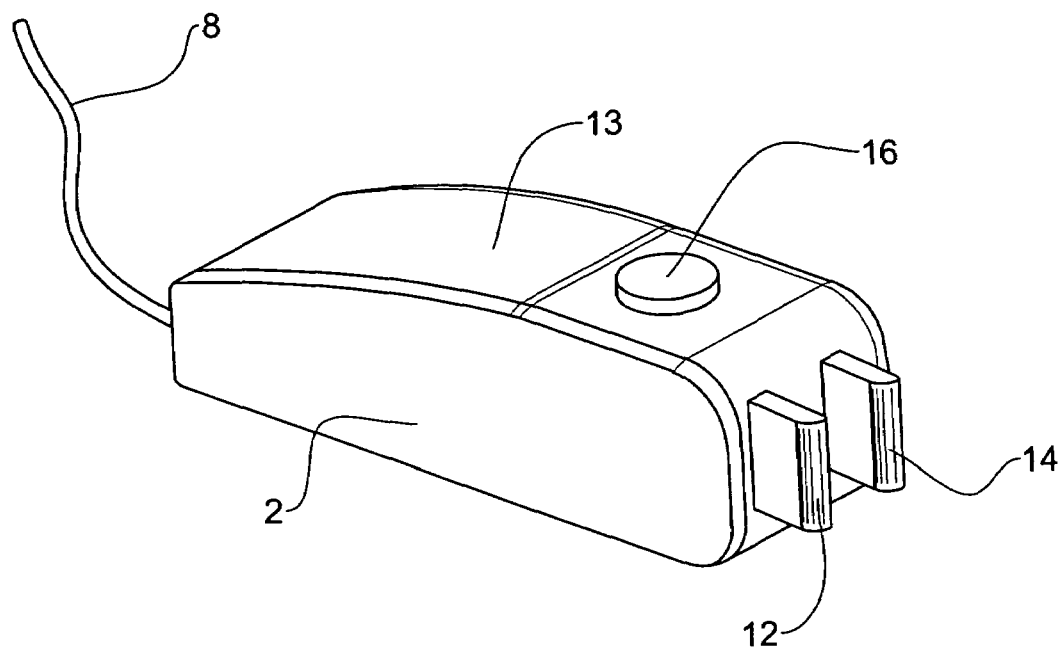
FIG. 2 shows the applicator of the system of FIG. 1.
Figure 3:
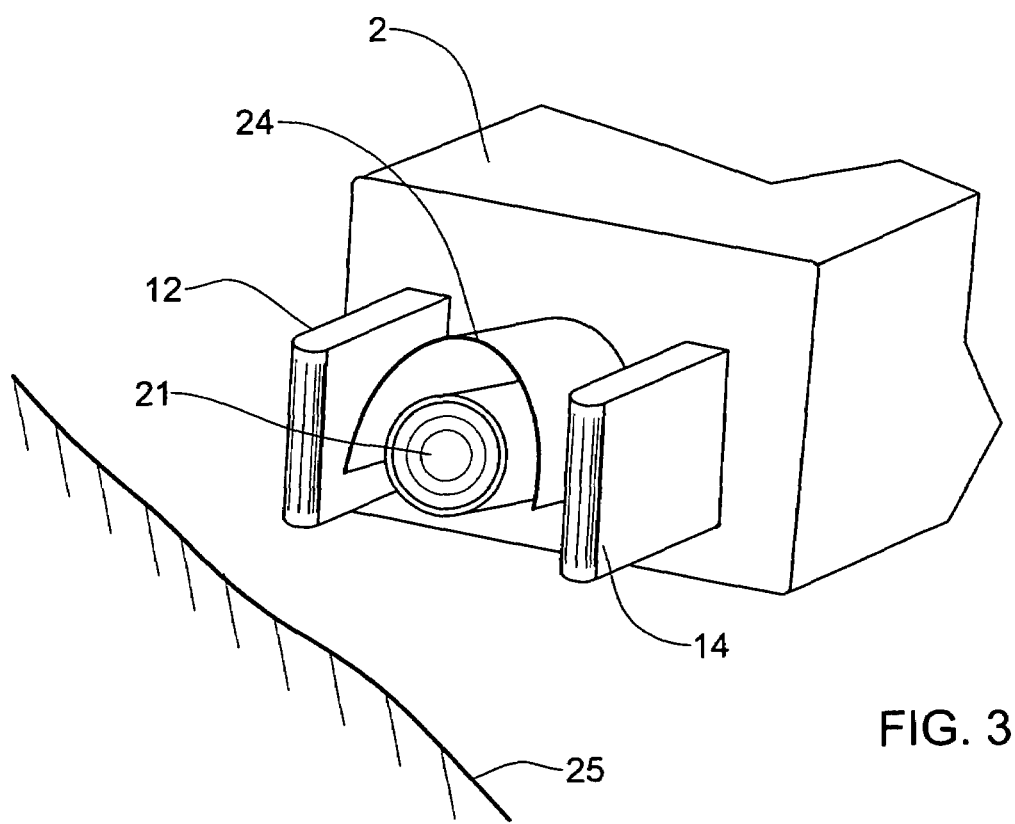
FIG. 3 shows the electrodes of the applicator of FIG. 2.

FIGS. 2 and 3 show the applicator 2 in greater detail. The applicator 2 contains a push-button on-off switch 16. The switch 16 is spring biased in an open position, so that no voltage is applied to the electrodes 12 and 14 when the switch 16 is released. When the applicator 2 is held by a user, as shown in FIG. 1, the switch 16 is depressed and a continuous or quasi-continuous wave RF voltage is applied between the electrodes 12 and 14. The electrodes 12 and 14 preferably have rounded edges in order to avoid hot spots on the skin surface in the vicinity of the edges of the electrodes. Rounded electrodes also allow smooth moving of the hand piece over the skin surface. A uni-polar electrode system may also be used (not shown).

The applicator 2 preferably, though not necessarily, includes a light source 21 which is located between the electrodes 12 and 14 that generates optical energy that is directed to the skin 25 surface by a reflector 24. Optical energy directed to the skin surface from the light source 21 is used to specifically heat pigmented targets at the skin surface. Such skin targets include vascular lesions, varicose veins, acne, and mole marks. The optical energy may have a single wavelength or several wavelengths. The wavelengths are selected to be optimal for the color of the contrasted component of the target, and are typically in the range of 400 to 1800 nm. A filament lamp or gas filled lamp can be used as the light source 21. Light from a laser or LED also can be used for skin irradiation.

In use, the applicator 2 is held by the user and the electrodes 12 and 14 are applied to the skin. The switch 16 is then depressed so as to deliver a continuous wave RF current to a section 17 of the skin between the electrodes 12 and 14. The applicator 2 is displaced over the skin in a skin region 15 to be treated so as to heat the skin region to a temperature that produces the desired treatment of the skin.

The displacement velocity of the applicator 2 over the skin is determined so that the skin section between the electrodes is heated to a temperature that produces the desired skin treatment, but does not damage the skin. Damage to the skin may include, for example, a first degree or higher burn, blisters, or blood coagulation. The displacement speed of the applicator over the skin will thus be a function of the continuous RF power. As the RF power increases, the movement of the applicator over the skin surface should be faster in order to avoid skin damage due to overheating of the skin.

The desired displacement speed can be determined, for example, using the equation $$V = \frac{P}{L d\, c\rho \Delta T},$$

where P is the power of the continuous RF current, L is the spacing of the electrodes, d is the penetration depth of the RF energy, c is the specific heat of the treated tissue, $\rho$ is the mass density of the tissue, and $\Delta T$ is the required temperature increase starting from am initial temperature equal to normal body temperature (about 37-39° C.). Thus, for example, if the RF power is P=5 W, the spacing of the electrodes is L=1 cm, the RF penetration depth is d=0.25 cm, $c\rho$=4 J/cm$^3$/°K and $\Delta T$=10° C., the applicator displacement speed should be about 0.5 cm/sec. in order to achieve the desired heating in amount of time in slightly more than 0.5 sec. If a mono-polar electrode system is used, the power should be lower to avoid damage to sub-dermal tissue.

A user treating his own skin with the system of the invention may simply displace the applicator over the skin surface in the region to be treated at a speed at which the user feels that the skin is heated but not to an extent that causes pain to the user. Alternatively, the control unit 6 may include a processor 7 that monitors the impedance of the skin between the electrodes 12 and 14. Since increasing skin temperature leads to a change in impedance, monitoring the skin impedance allows the temperature in the skin between the electrodes to be followed, as is known in the art. If the processor 7 determines that the skin temperature is below the range that is required to produce the desired skin treatment (for example, 45° C. to 60° C., which may be input to the processor prior to the treatment), the processor may generate a sensible signal, such as sounding an alarm 13 at a first pitch indicating to the user that the displacement speed should be decreased. Similarly, if the processor determines that the skin temperature is too high and may damage the skin, the processor can produce a second sensible signal, such as sounding the alarm 13 at a second pitch indicating to the user that the displacement speed should be increased.

The system 1 may be used with the following exemplary parameter values:

An RF power in the range of 2-10 Watts.
An energy delivery mode that is CW or Quasi-CW
An RF frequency in the range of 0.2-10 MHz
An optical energy spectrum in the range of 400-1800 nm
Optical energy power in the range of 1 to 20 Watts/cm$^2$

The invention claimed is:

1. A method for treating a skin surface region and a tissue volume under a skin surface region of an individual, said method comprising, for each of one or more locations in the region of the skin surface:

(a) applying a first electrode and a second electrode to the skin surface, first and second electrodes being spaced apart by a fixed distance L, at least the first electrode being applied to the location in the skin region;

(b) providing from the electrodes a continuous wave RF energy or a quasi-continuous wave RF energy to the tissue volume at the location, the RF energy having a power selected to heat the tissue volume at the location to the final temperature in an amount of time exceeding 0.5 sec; and (c) displacing the first and second electrodes over the skin surface at a displacement speed given by an algebraic expression $$V=P/Ldc\rho\Delta T,$$

where P is the power of the RF current, d is a penetration depth of the RE energy, c is a specific heat of the treated tissue, p is a mass density of the tissue, and $\Delta T$ is the required temperature increase.

2. The method according to claim 1 wherein the displacement speed is selected to heat the tissue volume to the final treatment temperature.

3. The method according to claim 1 wherein the RF energy has a power in the range of 2-10 W.

4. The method according to claim 1 wherein the RE power has a frequency in the range of 0.2-10 MHz.

5. The method according to claim 1 further comprising illuminating said skin surface located between the first electrode and a second electrode with optical energy of a selected wavelength.

6. The method according to claim 5 wherein the optical energy has a spectrum in the range of 400-1800 nm.

7. The method according to claim 5 wherein the optical energy has an energy power in the range of 1 to 10 W.

8. The method according to claim 5 wherein the light source is selected from an incandescent lamp, a gas filled lamp, a LED and a laser.

9. The method according to claim 1 further comprising determining a temperature at one or more locations in of the skin region volume.

10. The method according to claim 9 wherein the temperature is determined based upon one or more impedance measurements between the electrodes.

11. The method according to claim 1 further comprising increasing the displacement speed when the skin temperature at a location is above a predetermined temperature range.

12. The method according to claim 1 further comprising decreasing the displacement speed when the skin temperature at a location is below a predetermined temperature range.

13. The method according to claim 1 further comprising generating a first sensible signal if the skin temperature is below a predetermined temperature and a second sensible signal when the skin temperature is above a predetermined temperature range.

14. The method according to claim 1, wherein the skin treatment is selected from skin rejuvenation, collagen remodeling and contraction, skin tightening, wrinkle treatment, subcutaneous tissue treatment, cellulite treatment, pore size reduction, skin texture and tone improvement, acne treatment, skin vascular lesions, varicose veins, acne, mole marks, and hair removal.

15. The method according to claim 1 wherein the initial temperature is normal body temperature and wherein the predetermined treatment temperature, is the treatment temperature being in the range of 42° C.-60° C.

* * * * *